(12) United States Patent
Francke

(10) Patent No.: US 7,180,977 B2
(45) Date of Patent: Feb. 20, 2007

(54) SCANNING-BASED DETECTION OF IONIZING RADIAION FOR TOMOSYNTHESIS

(75) Inventor: Tom Francke, Sollentuna (SE)

(73) Assignee: Xcounter AB, Danderyd (SE)

( * ) Notice: Subject to any disclaimer, the term of this patent is extended or adjusted under 35 U.S.C. 154(b) by 121 days.

(21) Appl. No.: 11/104,573

(22) Filed: Apr. 13, 2005

(65) Prior Publication Data

US 2006/0210016 A1    Sep. 21, 2006

(30) Foreign Application Priority Data

Mar. 17, 2005   (SE) ................................. 0500610

(51) Int. Cl.
*A61B 6/00*        (2006.01)
(52) U.S. Cl. ....................... 378/23; 378/21; 378/22; 378/95
(58) Field of Classification Search ............ 378/21–26, 378/95
See application file for complete search history.

(56) References Cited

U.S. PATENT DOCUMENTS

| | | | |
|---|---|---|---|
| 4,466,113 A | 8/1984 | Strecker ...................... | 378/146 |
| 4,707,608 A | 11/1987 | DiBianca .................... | 250/389 |
| 4,780,897 A | 10/1988 | McDaniel et al. ............ | 378/62 |
| 4,800,580 A | 1/1989 | Houtman et al. ............. | 378/71 |
| 5,008,907 A | 4/1991 | Norman et al. ............... | 378/65 |
| 5,022,060 A | 6/1991 | Trotel .......................... | 378/19 |
| 5,025,376 A | 6/1991 | Bova et al. ................... | 378/28 |
| 5,126,938 A | 6/1992 | Oda ........................... | 378/13 |
| 6,067,342 A | 5/2000 | Gordon ....................... | 378/19 |
| 6,118,125 A | 9/2000 | Carlson et al. .......... | 250/385.1 |
| 6,118,841 A | 9/2000 | Lai ............................. | 378/19 |
| 6,243,438 B1 | 6/2001 | Nahaliel et al. .............. | 378/19 |
| 6,337,482 B1 | 1/2002 | Francke .................... | 250/385.1 |
| 6,353,227 B1 | 3/2002 | Boxen ...................... | 250/363.1 |

(Continued)

FOREIGN PATENT DOCUMENTS

DE    3035529 A1    5/1982

(Continued)

OTHER PUBLICATIONS

International Search Report dated Mar. 15, 2005.

(Continued)

*Primary Examiner*—Edward J. Glick
*Assistant Examiner*—Jurie Yun
(74) *Attorney, Agent, or Firm*—Harness, Dickey & Pierce, P.L.C.

(57) ABSTRACT

A scanning-based apparatus for obtaining tomosynthesis data of an object performing a periodic movement comprises a radiation source emitting radiation around an axis of symmetry; a radiation detector comprising line detectors, each being directed towards the divergent radiation source to allow a ray bundle of the radiation that propagates in a different angle to enter the line detector after having been transmitted through the object, and to be detected repeatedly therein; and a movement device provided for moving the radiation source and the radiation detector relative to the object linearly in a path orthogonal to the symmetry axis, and a distance which is sufficient for scanning each of the line detectors across the entire object. The movement device is provided to repeat the movement a plurality of times, each time with a different phase shift relative to the periodic movement of the object.

20 Claims, 4 Drawing Sheets

U.S. PATENT DOCUMENTS

| | | | |
|---|---|---|---|
| 6,373,065 B1 | 4/2002 | Francke et al. | 250/374 |
| 6,385,282 B1 | 5/2002 | Francke et al. | 278/51 |
| 6,414,317 B1 | 7/2002 | Francke et al. | 250/385.1 |
| 6,476,397 B1 | 11/2002 | Francke | 250/385.1 |
| 6,477,223 B1 | 11/2002 | Francke | 378/19 |
| 6,518,578 B1 | 2/2003 | Francke et al. | 250/374 |
| 6,522,722 B1 | 2/2003 | Francke | 378/146 |
| 6,546,070 B1 | 4/2003 | Francke | 378/51 |
| 6,600,804 B2 | 7/2003 | Francke et al. | 378/51 |
| 6,628,745 B1 | 9/2003 | Annis et al. | 378/21 |
| 6,731,065 B1 | 5/2004 | Francke et al. | 313/532 |
| 6,784,436 B2 | 8/2004 | Francke | 250/385.1 |
| 6,794,656 B2 | 9/2004 | Francke et al. | 250/385.1 |
| 6,940,942 B2 * | 9/2005 | Ullberg | 378/26 |
| 2002/0003860 A1 | 1/2002 | Francke et al. | 378/98.8 |
| 2003/0155519 A1 | 8/2003 | Francke et al. | 250/385.1 |
| 2004/0120450 A1 | 6/2004 | Flohr et al. | 378/4 |
| 2005/0213701 A1 * | 9/2005 | Sendai | 378/8 |

FOREIGN PATENT DOCUMENTS

| | | |
|---|---|---|
| DE | 10235849 A1 | 3/2004 |
| EP | 0244292 A1 | 11/1987 |
| GB | 2070883 | 2/1981 |
| GB | 2061055 | 5/1981 |
| WO | WO 00/62094 | 10/2000 |
| WO | WO 01/59480 | 8/2001 |
| WO | WO 2005002443 A1 | 1/2005 |

OTHER PUBLICATIONS

International Search Report dated Mar. 17, 2005.

* cited by examiner

SCANNING-BASED DETECTION OF IONIZING RADIAION FOR TOMOSYNTHESIS

FIELD OF THE INVENTION

The invention relates generally to scanning-based apparatuses and methods for obtaining time-resolved tomosynthesis data for examination of an object, which performs a periodic movement, such as e.g. heart beats.

BACKGROUND OF THE INVENTION AND RELATED ART

In tomosynthesis imaging a plurality of images of radiation that has passed through an object is acquired at different angles. By combining the plurality of images, it is possible to reconstruct any plane in the irradiated object. The higher number of images is utilized, the better image quality in the reconstructed tomosynthesis images is obtained. The larger angle over which the images are acquired, the better position resolution in the direction orthogonal to the detector plane.

WO 2005/002443 A1 discloses an apparatus for obtaining tomosynthesis data of an object comprising a source emitting radiation centered around an axis of symmetry; a radiation detector comprising a stack of line detectors, each being directed towards the source at a respective angle; and a device for moving the source and the radiation detector relative to the object linearly in a direction orthogonal to the symmetry axis, while each of the line detectors is adapted to record line images of radiation as transmitted through the object in the respective angle. A two-dimensional image is produced at a separate angle by each of the line detectors.

Such apparatus is known to produce tomosynthesis data of an object at higher speed than what is obtainable by using single one-dimensional detectors, which makes the measurement less time consuming.

SUMMARY OF THE INVENTION

However, in some situations the temporal resolution is still unsatisfying. The temporal resolution is set by the time it takes for a single line detector to scan over the entire object. Given an object, such as e.g. a heart, that measures about 20 cm in the scanning direction, and assuming a scanning speed of 6 m/s, the temporal resolution of a two-dimensional tomosynthesis image is about 30 ms. In case of periodically moving objects such temporal resolution is typically insufficient.

A main object of the invention is therefore to provide a scanning-based apparatus and a method, respectively, for obtaining tomosynthesis data of an object, which performs a periodic movement, by which series of two-dimensional tomosynthesis images of higher temporal resolution and at higher repetition rate can be recorded.

A further object of the invention is to provide such an apparatus and such a method, which are uncomplicated and can produce high-quality highly time-resolved two-dimensional tomosynthesis images with high spatial resolution, high signal-to-noise ratio, high dynamic range, high image contrast, and low noise from overlaying tissue.

A yet further object of the invention is to provide such an apparatus and such a method, which are reliable, accurate, precise, and relatively inexpensive.

These objects, among others, are attained by apparatuses and methods as claimed in the appended claims.

The inventors have found that by providing a scanning-based apparatus for obtaining tomosynthesis data of an object performing a periodic movement, which apparatus comprises (i) a radiation source provided for emitting radiation centered around a symmetry axis; (ii) a radiation detector comprising line detectors, each being directed towards the radiation source to allow a ray bundle of the radiation that propagates in a respective different angle to enter the line detector, and each line detector being provided for repeatedly recording a one-dimensional image of the ray bundle entered into the line detector; (iii) an object area arranged in the radiation path between the radiation source and the radiation detector for holding the object; and (iv) a movement device provided for moving the radiation source and the radiation detector relative to the object essentially linearly along a path essentially orthogonal to the symmetry axis, and a distance which is sufficient for scanning each of the line detectors across the entire object, wherein the movement device is provided for moving the radiation source and the radiation detector relative to the object the distance along the path a plurality of times, each time with a different phase shift relative to the periodic movement of the object, series of two-dimensional tomosynthesis images of higher temporal resolution can be recorded by each line detector at higher repetition rate.

Preferably, the movements of the radiation source and the radiation detector relative to the object (scans of the object) are synchronized with the periodic movement of the object. The scans are advantageously performed in successive periods of the periodic movement of the object, and alternately in opposite directions.

The phase shifts are advantageously substantially evenly distributed over the period of the periodic movement of the object. By combining data from different two-dimensional images of each line detector to form two-dimensional images formed by measurements in different periods of the periodic movement of the object, the temporal resolution can be increased by a factor, which is equal to the number of scans performed.

The line detectors used are preferably, but not exclusively, direction-sensitive gaseous-based parallel plate detectors. Other line detectors that may be used include scintillator-based arrays, CCD arrays, TFT- and CMOS-based detectors, liquid detectors, and diode arrays, e.g. PIN-diode arrays with edge-on, near edge-on or perpendicular incidence of X-rays. A collimator structure may be arranged in front of the detectors to partly reject scattered X-rays.

Further characteristics of the invention and advantages thereof, will be evident from the detailed description of embodiments of the present invention given hereinafter and the accompanying FIGS. 1–6, which are given by way of illustration only and thus, are not limitative of the present invention.

DESCRIPTION OF EMBODIMENTS

Figure 1:
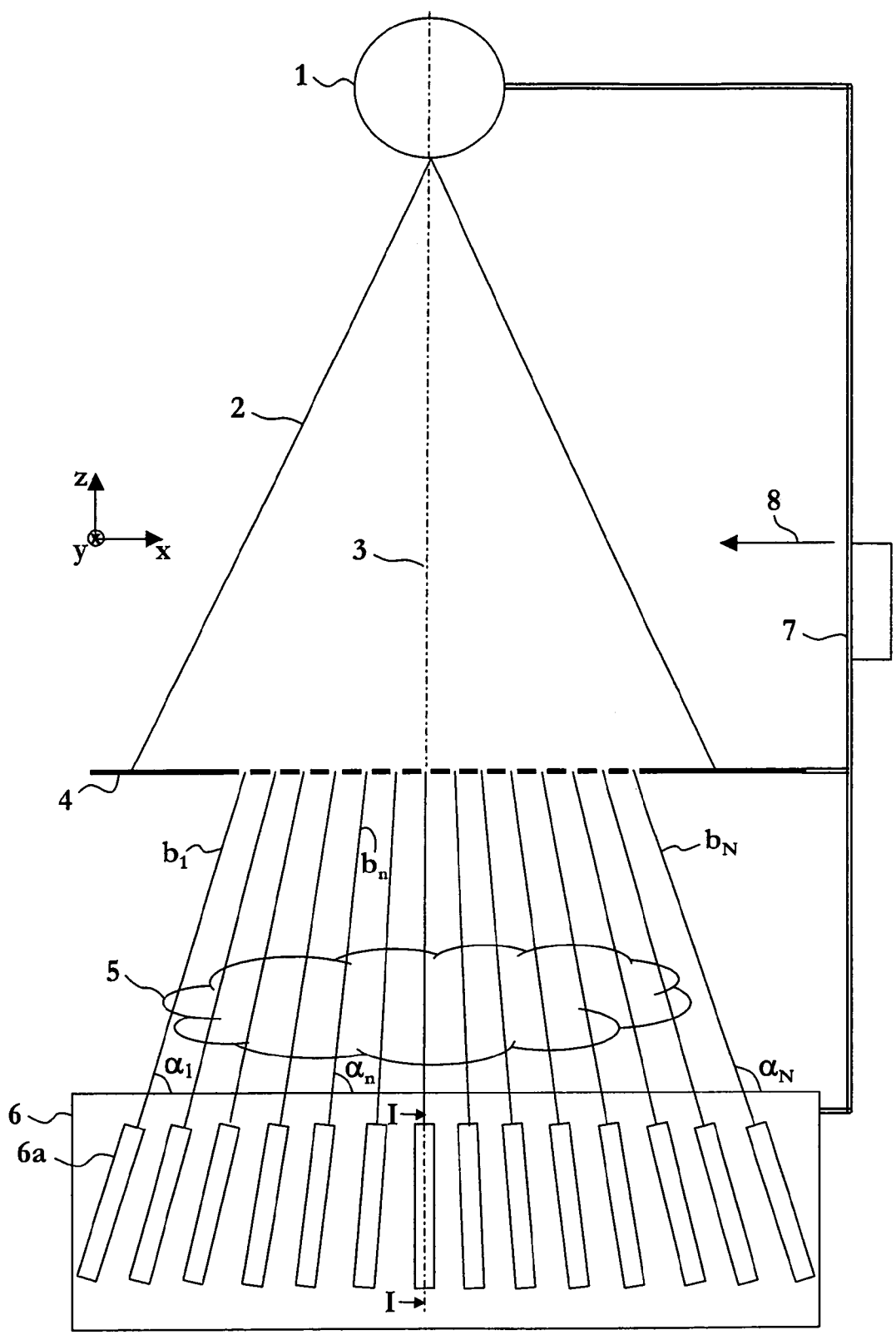
FIG. 1 illustrates schematically, in a top view, an apparatus for obtaining tomosynthesis data of an object according to the present invention.

The apparatus of FIG. 1 comprises a divergent X-ray source 1, which produces X-rays 2 centered around an axis of symmetry 3 (parallel with the z axis), a collimator 4, a radiation detector 6, and a device 7 for rigidly connecting the X-ray source 1, the collimator 4, and the radiation detector 6 to each other and moving the X-ray source 1, the collimator 4, and the radiation detector 6 essentially linearly in direction 8 (typically parallel with the x axis) essentially orthogonal to the axis of symmetry 3 to scan an object 5, which is to be examined. In the present invention the object 5 performs a periodic movement. It may for instance be a heart beating or a lung periodically filled with and emptied of air.

The radiation detector 6 comprises a stack of line detectors 6a, each being directed towards the divergent radiation source 1 to allow a respective ray bundle $b1, \ldots, b_n, \ldots, b_N$ of the radiation 2 that propagates in a respective one of a plurality of different angles $\alpha_1, \ldots, \alpha_n, \ldots, \alpha_N$ with respect to the front surface of the radiation detector 6 to enter the respective line detector 6a. The line detectors 6a are extending in the y direction to record line images extending in the y direction.

The collimator 4 may be a thin foil of e.g. tungsten with narrow radiation transparent slits cut away, the number of which corresponds to the number of line detectors 6a of the radiation detector 6. The slits are aligned with the line detectors 6a so that X-rays passing through the slits of the collimator 4 will reach the detector units 6a, i.e. as the respective ray bundles $b_1, \ldots, b_n, \ldots, b_N$. The collimator 4, which is optional, prevents radiation, which is not directed directly towards the line detectors 6a, from impinging on the object 5, thereby reducing the radiation dose to the object. This is advantageous in all applications where the object is a human or an animal, or parts thereof.

During scanning the device 7 moves the radiation source 1, the collimator 4, and the radiation detector 6 relative to the object 5 in a linear path parallel with the front of the radiation detector as being indicated by arrow 8, while each of the line detectors 6a repeatedly records a line image of radiation as transmitted through the object 5 in a respective one of the different angles $\alpha_1, \ldots, \alpha_n, \ldots, \alpha_N$.

The scanning of the object 5 is performed a length, which is sufficiently large so that each one of the line detectors 6a can be scanned across the entire object of interest to obtain, for each of the line detectors 6a, a two-dimensional image of radiation as transmitted through the object 5 in a respective one of the different angles $\alpha_1, \ldots, \alpha_n, \ldots, \alpha_N$.

Figure 2A:
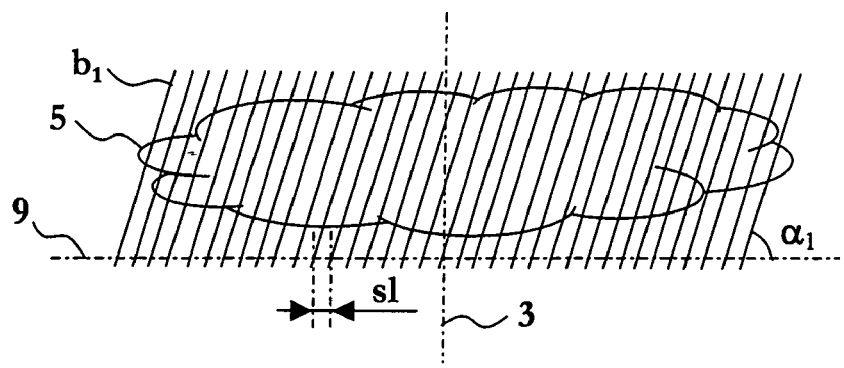
FIGS. 2a–c illustrate each schematically, in a top view, a particular X-ray bundle as it traverses the examination object during a first scanning movement by the apparatus of FIG. 1.
Figure 2B:
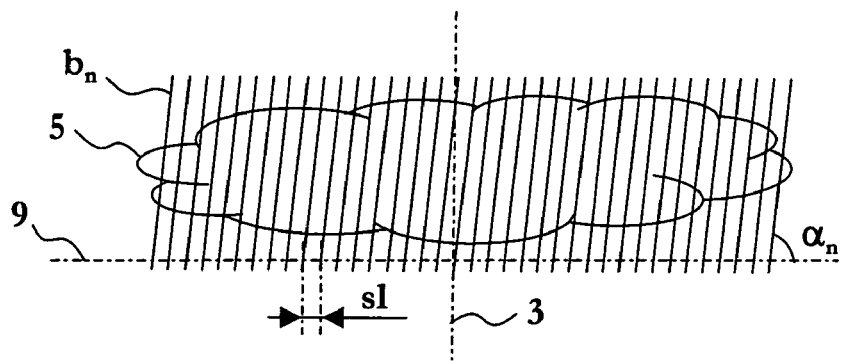
Figure 2C:
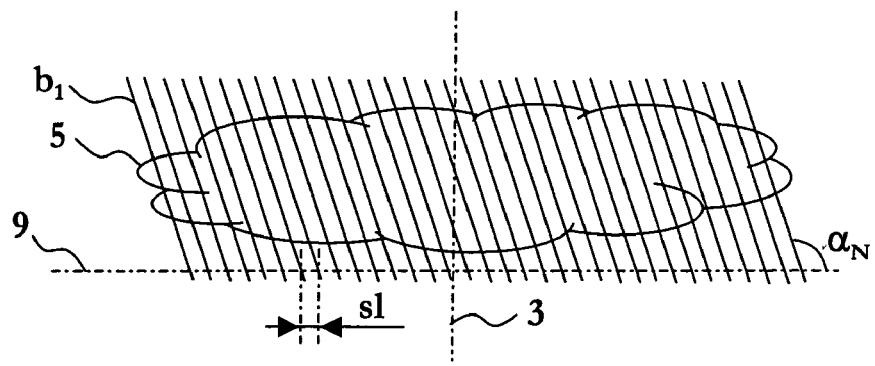

In FIGS. 2a–c three different X-ray bundles $b_1, b_n,$ and $b_N$ are schematically illustrated as they traverse the examination object 5 during scanning by the apparatus of FIG. 1. Reference numeral 9 indicates a plane parallel with the x axis, which coincides with the scanning direction 8 and with the front of the radiation detector 2.

As can be seen in FIGS. 2a–c each line detector/X-ray bundle pair produces a complete two-dimensional image at a distinct one of the different angles. FIG. 2a illustrates the formation of a two-dimensional image of radiation transmitted through the object at an angle $\alpha_1$, FIG. 2b illustrates the formation of a two-dimensional image of radiation transmitted through the same object, but at an angle $\alpha_n$, and FIG. 2c illustrates the formation of a similar two-dimensional image, but at an angle $\alpha_N$.

Preferably, the different angles are distributed over an angular range $\alpha_N$–$\alpha_1$ of at least 5°, preferably at least 10°, and most preferably at least 15° depending on the application or kind of examination in order to obtain high-quality tomosynthesis data for examination of the object. The number of line detectors 6a in the stack of line detectors is at least 3, preferably at least 10, and most preferably at least 25 depending on the number of images recorded at different angles, which is required during the examination.

The scanning step, in FIGS. 2a–c denoted by sl, depends on the desired spatial resolution of the two-dimensional images formed from the one-dimensional recordings. Typically, the scanning step sl can be about 10–500 micrometers and the individual detecting elements of each of the line detectors can be of similar size.

For an exemplary detector comprising 100 line detectors with a pitch of 1 cm, the length (in the scanning direction) of the detector will be 1 m. Given an object extending about 0.2 m in the scanning direction, the complete scanning length will be 1.2 m to allow each of the line detectors to be scanned over the entire object. Given a total scanning time of 0.2 s, limited by e.g. X-ray fluence from the X-ray tube or readout time in the electronics, the scanning speed will be about 6 m/s, and the line detectors are read out repeatedly during the scan to record 100 two-dimensional images of the object 5, each at a separate angle.

The temporal resolution will be given by the time taken for each line detector scanning 0.2 m, which is about 30 ms. For an object, which performs a movement, i.e. a periodic movement, this resolution may not be sufficient.

Thus, according to the present invention the movement device 7 is provided, while the line detectors 6a repeatedly detect line images, for moving the radiation source 1, the collimator 4, and the radiation detector 6 relative to the object 5 the above-identified distance along the linear path a plurality of times, each time with a different phase shift relative to the periodic movement of the object 5, to obtain, for each of the line detectors 6a, a plurality of two-dimensional images of radiation as transmitted through the object 5 in a respective one of the different angles.

FIGS. 3–6 illustrate schematically, in top views, an inventive apparatus during different stages of scanning. The apparatus is similar to the apparatus of FIG. 1, but comprises also a device 31 for measuring the periodic movement of the object 5, and a computer 33 provided for synchronizing the movements of the radiation source 1, the collimator 4, and the radiation detector 6 relative to the object 5.

In the case the object 5 is a heart, the device 31 for measuring the periodic movement may be an ECG device or a device for measuring pressure variations in veins or arteries.

The computer 33 may comprise modules for post-processing recorded data and be provided for displaying two-dimensional images of a slice through the object 5 as formed in a tomosynthesis reconstruction process, either as separate images or as a movie of the periodic movement such as heart beats.

Figure 3:
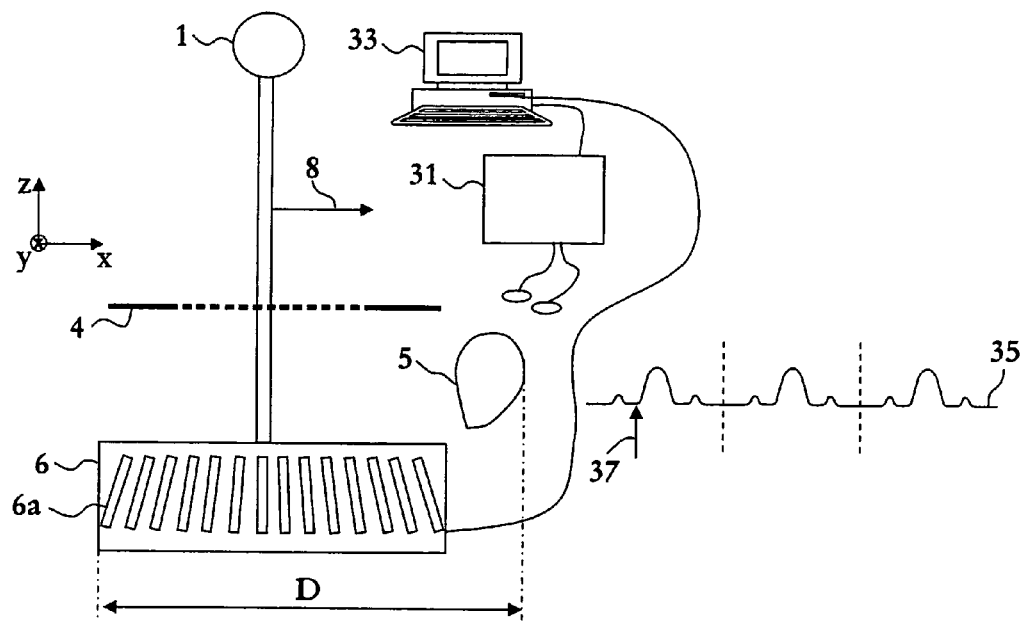
FIGS. 3–6 illustrate schematically, in top views, an apparatus for obtaining tomosynthesis data of an object according to the invention during different stages of scanning.

FIG. 3 illustrates the inventive apparatus at the beginning of the scanning. The line detector at the right hand end of the radiation detector 6 is just to begin recording the transmission of the X-rays through a heart 5. The periodic movement is indicated by an ECG diagram 35 showing three heart beats. Scanning starts at the time indicated by arrow 37, and the scanning direction is indicated by arrow 8.

Figure 4:
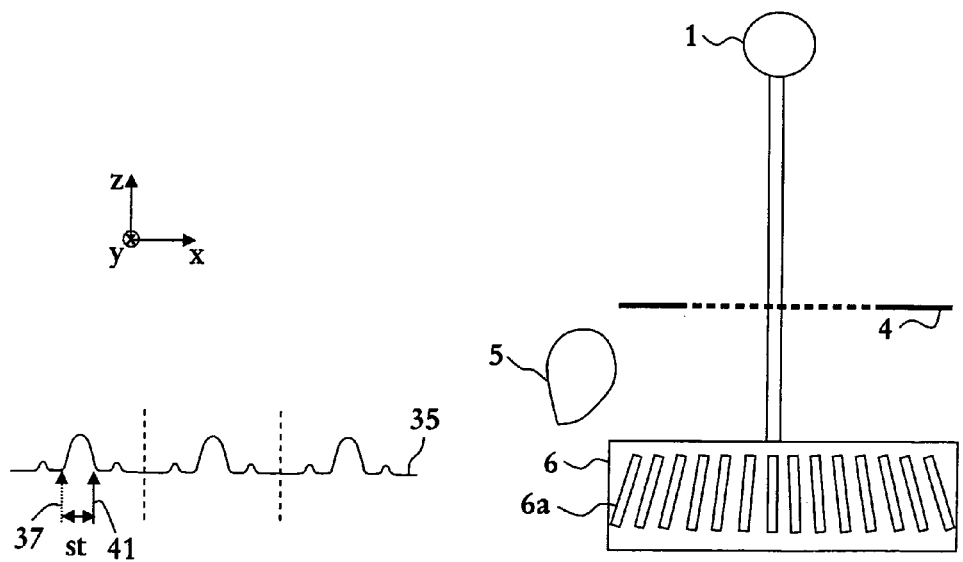

FIG. 4 illustrates the inventive apparatus at the end of a first scanning movement of the scanning. The apparatus has been scanned a distance D being the sum of the dimensions of the radiation detector 6 and the heart 5 in the direction of the scanning, and the line detector at the left hand end of the radiation detector 6 has just terminated to record the transmission of the X-rays through the heart 5. The first scanning movement is ended at the time indicated by arrow 41, and the scanning time for the first scanning movement is indicated by st. This time is preferably considerably shorter than the period of the movement of the heart.

Figure 5:
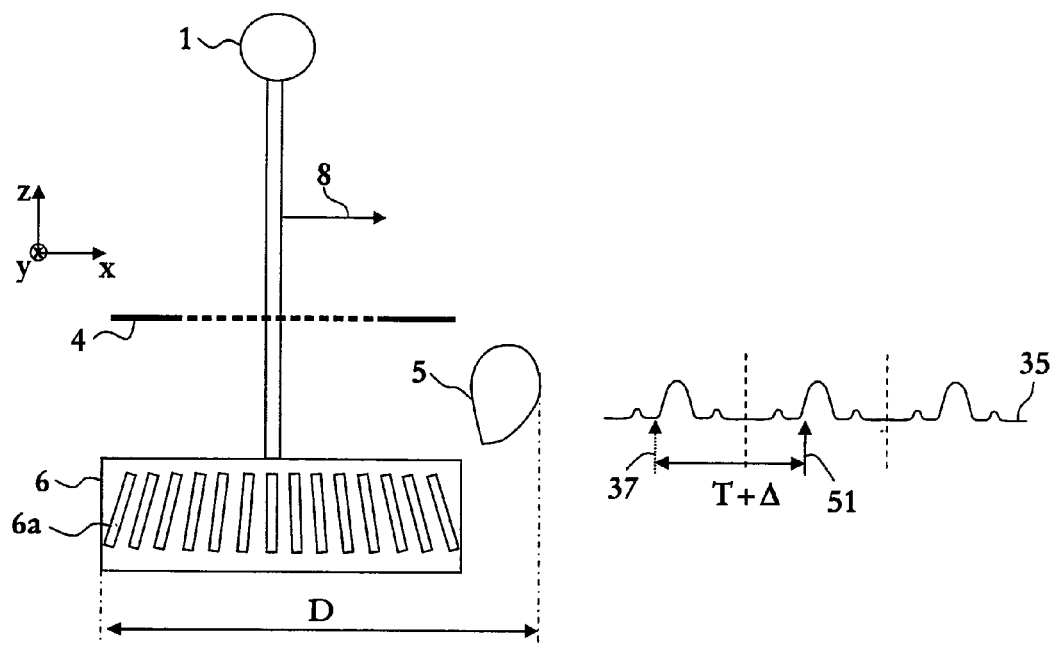

FIG. 5 illustrates the inventive apparatus at the beginning of a second scanning movement of the scanning. The line detector 6a at the right hand end of the radiation detector 6 is again just to begin recording the transmission of the X-rays through the heart 5. The second scanning movement starts at the time indicated by arrow 51, which is at a time T+Δ after the beginning of the first scanning movement, wherein T is the period of the movement and α is a small phase shift.

Figure 6:
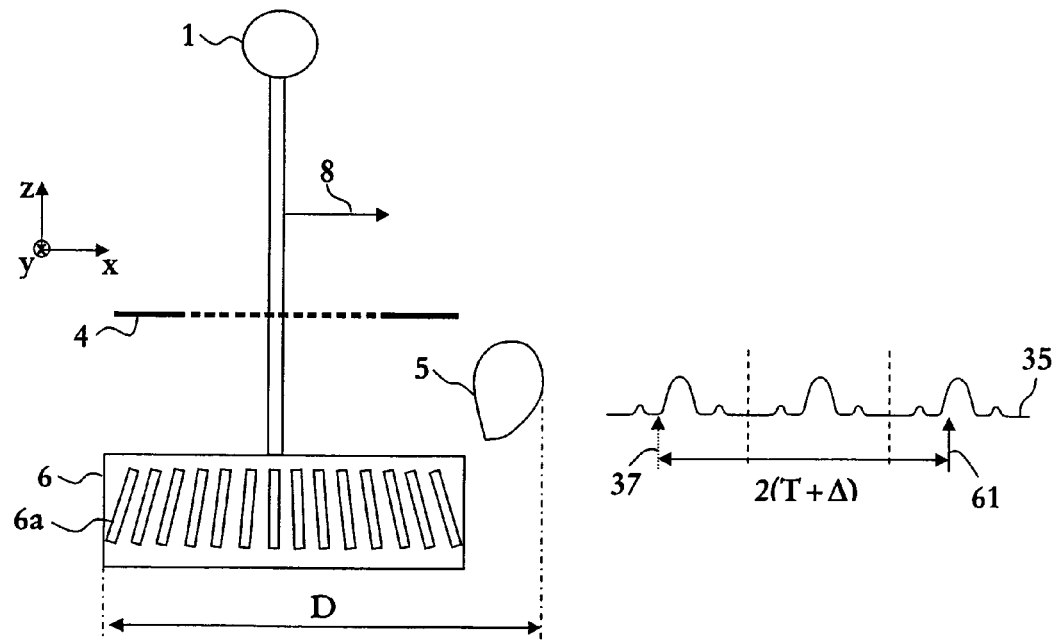

FIG. 6, finally, illustrates the inventive apparatus at the beginning of a third scanning movement of the scanning. The line detector 6a at the right hand end of the radiation detector 6 is again just to begin recording the transmission of the X-rays through the heart 5. The third scanning movement starts at the time indicated by arrow 61, which is at a time 2(T+Δ) after the beginning of the first scanning movement.

The scanning comprises further scanning movements, each time in a new period of the movement of the heart and each time with a further phase shift of Δ. This continues until the sum of the phase shifts ΣΔ reaches a full period T. Then the scanning is completed.

Advantageously, but not necessarily, the phase shifts are substantially evenly distributed over the period of the periodic movement of the object 5. Similarly, the movements of the radiation source 1, the collimator 4, and the radiation detector 6 relative to the object 5 are advantageously, but not necessarily, performed under successive periods of the periodic movement of the object 5.

However, it is practically if the apparatus has not to be returned to its initial state after each scanning movement. Thus, the scanning movements may be performed alternately in opposite directions so the radiation detector 6 is scanned back and fourth over the object 5.

The computer 33 performing the tomosynthesis reconstruction process may form each of the two-dimensional images of radiation, on which the reconstruction is based, from line images recorded during different ones of the scanning movements. For instance, each of the two-dimensional images of radiation may be obtained from K/N line images recorded during each of the scanning movements, where K is the number of line images recorded by each of the line detectors during each of the scanning movements, and N is the number of scanning movements performed during the scanning.

Alternatively, the computer 33 bases the tomosynthesis reconstruction process on two-dimensional images of radiation, of which each is formed from line images recorded during a single one of the scanning movements.

The number of scanning movements gives the number of two-dimensional images formed in the reconstruction process that can be used for studying the time development of the periodic movement.

What is claimed is:

1. A scanning-based apparatus for obtaining tomosynthesis data of an object performing a periodic movement comprising:
    a divergent radiation source provided for emitting radiation centered around an axis of symmetry;
    a radiation detector comprising a stack of line detectors, each line detector being directed towards the divergent radiation source to allow a ray bundle of said radiation that propagates in a respective one of a plurality of different angles to enter the line detector, and being provided for repeatedly recording a one-dimensional image of the ray bundle entered into the line detector;
    an object area arranged in the radiation path between said divergent radiation source and said radiation detector for housing said object; and
    a movement device provided for moving said divergent radiation source and said radiation detector relative to said object essentially linearly along a path essentially orthogonal to said axis of symmetry, and a distance which is sufficient for scanning each of said line detectors across the entire object, while the line detectors repeatedly detect line images, wherein
    said movement device, while the line detectors repeatedly detect line images, moves the divergent radiation source and the radiation detector relative to the object said distance along said path a plurality of times, each time with a different phase shift relative to the periodic movement of said object, to obtain, for each of said line detectors, a plurality of two-dimensional images of radiation as transmitted through said object in a respective one of said plurality of different angles, said two-dimensional images constituting said tomosynthesis data.

2. The scanning-based apparatus of claim 1 wherein said phase shifts are substantially evenly distributed over the period of said periodic movement of said object.

3. The scanning-based apparatus of claim 1 wherein said movement device is provided for moving the divergent radiation source and the radiation detector relative to the object said distance along said path alternately in opposite directions.

4. The scanning-based apparatus of claim 1 wherein each of said plurality of two-dimensional images of radiation is obtained from line images recorded during different ones of the movements of the divergent radiation source and the radiation detector relative to the object.

5. The scanning-based apparatus of claim 4 wherein each of said plurality of two-dimensional images of radiation is obtained from K/N line images recorded during each one of the movements by said movement device, K being the number of line images recorded by each of the line detectors during each of the movements by said movement device, and N being the number of movements made by said movement device.

6. The scanning-based apparatus of claim 1 wherein said object is a heart.

7. The scanning-based apparatus of claim 6 further comprising
    a device for measuring the periodic movement of said object; and
    a device provided for synchronizing the plurality of movements of the divergent radiation source and the radiation detector relative to the object said distance along said path with said periodic movement of said object.

8. The scanning-based apparatus of claim 7 wherein said device for measuring the periodic movement of said object is an ECG device or a device for measuring pressure variations in veins or arteries.

9. The scanning-based apparatus of claim 1 wherein
    each of said movements of the divergent radiation source and the radiation detector relative to the object is performed in a time less than one period of said periodic movement of said object; and said movements of the divergent radiation source and the radiation detector relative to the object are performed under successive periods of said periodic movement of said object.

10. The scanning-based apparatus of claim 1 wherein the dimension of said detector in the direction of said movement is longer, preferably at least two times longer, than the dimension of said object in the direction of said movement.

11. The apparatus of claim 1 wherein
said divergent radiation source is an X-ray source; and
said line detectors are each a gaseous-based ionization detector, wherein electrons freed as a result of ionization by a respective ray bundle are accelerated in a direction essentially perpendicular to the direction of that ray bundle.

12. The apparatus of claim 11 wherein said gaseous-based ionization detector is an electron avalanche detector.

13. The apparatus of claim 11 wherein said gaseous-based ionization detector is formed to be highly directions sensitive.

14. The apparatus of claim 1 wherein said line detectors are each any of a diode array, a scintillator-based array, a CCD array, a TFT- or CMOS-based detector, or a liquid detector.

15. The apparatus of claim 1 comprising a collimator arranged in the radiation path between said radiation source and said object area, said collimator preventing radiation, which is not directed towards said line detectors, from impinging on said object, thereby reducing the radiation dose to said object.

16. A method for obtaining tomosynthesis data of an object comprising the steps of:
emitting radiation centered around an axis of symmetry by a divergent radiation source;
directing a radiation detector comprising a stack of line detectors towards the divergent radiation source so that each line detector is directed towards the divergent radiation source to allow a ray bundle of said radiation that propagates in a respective one of a plurality of different angles to enter the line detector;
arranging the object, which performs a periodic movement, in the radiation path between said divergent radiation source and said radiation detector; and
moving said divergent radiation source and said radiation detector relative to said object essentially linearly along a path essentially orthogonal to said axis of symmetry, and a distance which is sufficient for scanning each of said line detectors across the entire object, while each of said line detectors records repeatedly the ray bundle entered into the line detector after having been transmitted through the object, said method further comprising the steps of:

while the line detectors repeatedly record the ray bundles entered into the line detectors after having been transmitted through the object, moving the divergent radiation source and the radiation detector relative to the object said distance along said path a plurality of times, each time with a different phase shift relative to the periodic movement of said object; and
forming, for each of said line detectors, a plurality of two-dimensional images of radiation as transmitted through said object in a respective one of said plurality of different angles, said two-dimensional images constituting said tomosynthesis data.

17. The method of claim 16 wherein each of said plurality of two-dimensional images of radiation is formed from line images recorded during different ones of the movements of the divergent radiation source and the radiation detector relative to the object.

18. A scanning-based tomosynthesis apparatus for obtaining images of an object performing a periodic movement, the tomosynthesis apparatus comprising:
a radiation source, which emits radiation;
a radiation detector comprising a plurality of line detectors, each line detector being directed towards the radiation source, and repeatedly recording a one-dimensional image of radiation as transmitted through said object and subsequently entered into the line detector; and
a movement device which, while the line detectors repeatedly detect line images, moves the radiation source and the radiation detector relative to the object a plurality of times, each time essentially linearly a distance, which is sufficient for scanning each of said line detectors across the entire object, and each time with a different phase shift relative to the periodic movement of said object, to obtain, for each of said line detectors, a plurality of two-dimensional images of radiation as transmitted through said object in a separate one of a plurality of different angles.

19. The apparatus of claim 18 comprising a post-processing device for treating said plurality of two-dimensional images in a tomosynthesis reconstruction process to obtain a plurality of time-shifted two-dimensional images of a plane in the irradiated object to thereby allow for the studying of the time development of the periodic movement of said object.

20. The apparatus of claim 19 comprising a device displaying said plurality of time-shifted two-dimensional images one after another to obtain a motion picture of the periodic movement of said object.

* * * * *